US00PP07935P

United States Patent [19]

Hanes

[11] Patent Number: Plant 7,935

[45] Date of Patent: Aug. 11, 1992

[54] GERANIUM NAMED AMERICANA CHERRY RED

[75] Inventor: Mitchell Hanes, Morgan Hill, Calif.

[73] Assignee: Goldsmith Seeds, Inc., Gilroy, Calif.

[21] Appl. No.: 656,706

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new and distinctive Geranium cultivar particularly distinguished by its cherry red colored semi-double flowers, its green foliage and its vigorous growth and its superior cutting productivity.

1 Drawing Sheet

BACKGROUND OF THE NEW PLANT

The present invention comprises a new and distinct cultivar of Geranium, botanically known as *Pelargonium hortorum* Bailey. This new cultivar is propagated from a seedling resulting from the cross of a single flowered, cherry-red colored inbred line known as line number 966A-2 by a red colored semi-double flowered inbred pollen parent known as 58-1.

This cultivar is a product of a planned breeding program intended to create new geranium cultivars with cherry-red colored flowers, semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed descriptions set forth the distinctive characteristics of this Geranium cultivar. The data which defines these characteristics were collected from asexual reproductions carried out by Goldsmith Seeds, Inc. in Gilroy, Calif. The plant history was taken on 20 week old plants, grown in 5½ inch pots blossomed under natural light in a greenhouse. Color readings were taken in the greenhouse on May 29, 1990 at 2 P.M. under ambient light. Color references are primarily to The RHS Colour Chart of The Royal Horticultural Society of London, England.

THE PLANT

Classification:

*Botanical.*—*Pelargonium hortorum* Bailey.

*Commercial.*—Zonal geranium.

Form: Compact bush.

Height: Nine to twelve cm. as a 5½ inch pot plant, excluding blooms.

Growth: Mounded habit, free flowering.

Strength: Strong basally branching plant that is resistant to rain and wind damage. Good shipping ability as rooted or unrooted cuttings.

Foliage: Abundant quantity.

Leaves:

*Size.*—Diameter about 6–8 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 2.5 to 5.0 cm. long.

*Color.*—Upper side: Green. Underside: Lighter green color. Ribs and veins not prominently different from upper surface.

Petioles: About 4 to 6 cm. in length.

THE BUD

Size:

*Diameter.*—About 7 mm.

*Length.*—About 1.5 cm. to 1.9 cm. at time of bud opening.

Shape: Pointed ovoid.

Color: Of petals when sepals first divide, RHS 57-D.

Sepals: Five in number, flat behind petals, pointed linear lanceolate, RHS 143-C in an open flower.

THE FLOWER

Blooming habit: Continuous throughout the year.

Size: Approximately 4.5–5.0 cm. diameter, 0.5 cm. deep, irregularly radially symmetrical.

Form: Irregularly shaped when bloom first opens, later flattening with maturity.

Petals: Five to six imbricate outer petals, 1.8–2.2 cm. wide and approximately 2.1–2.5 cm. long, 2 to 6 inner smaller petaloids of varying shape. Both the outer petals and inner petaloids are cherry-red 45-B in color. Veins same color as the interveinal regions. Color changing little with age. Underside of petals slightly lighter color. Petals and petaloids soft and satiny.

Pedicel: Approximately 1.5–2.0 cm. in length.

Persistence: Nonshattering flower.

INFLORESCENSE

Type: An umbel composed of approximately 30 flowers, erect laterally ascending.

Peduncle: Approximately 11.5–14 cm. in length, mostly 13 cm.; green with very faint red speckles on the oldest peduncles on the side of the peduncle that faces the sun.

REPRODUCTIVE ORGANS

Stamens:

*Anthers.*—Five to ten positioned below the mature stigma, dull red prior to anthesis.

*Filaments.*—All are white near base, individual filaments vary, some display a pink color on the mid-section to distal end while others display a red stripe through this area, all are reddish at the area where the anther attaches.

*Pollen.*—Orange in color.

Pistil:

*Number.*—One.

*Stigma.*—Five (sometimes six) linear lobes of near equal length, curling back toward ovary, purplish-red.

Style:

*Length.*—About 3.0–3.5 mm., color: purplish-red.

Ovaries: At anthesis, densely pubescent with white hairs, oblong. Green drying to a light brown at maturity.

Fruit: Partially fertile.

I claim:

1. A new and distinct cultivar of Geranium substantially as herein shown and described, characterized by its green foliage, cherry-red colored semi-double flowers on intermediate sized umbels, the plant being fast-rooting and free flowering with a compact growth habit.

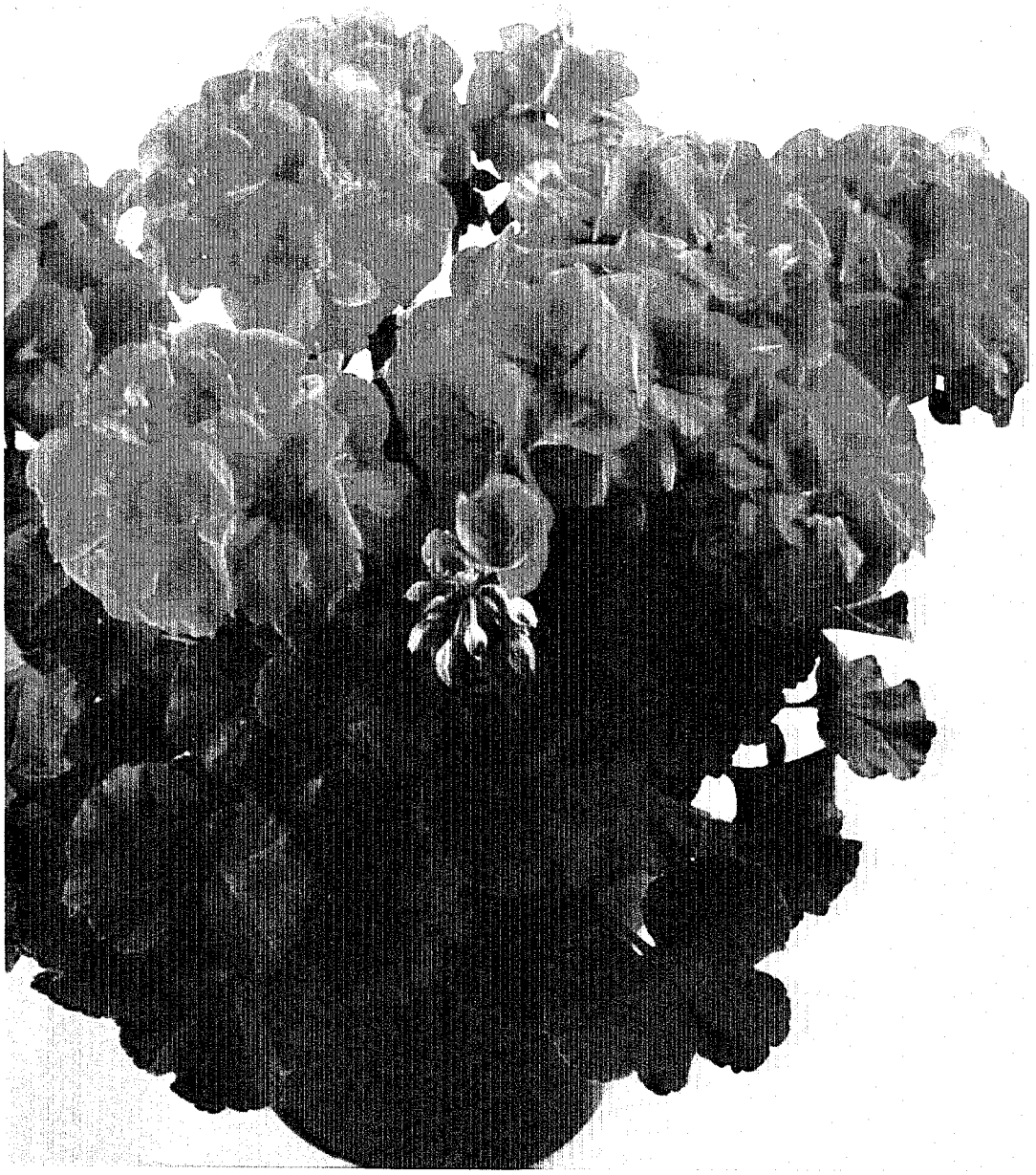

* * * * *